United States Patent [19]

Harju-Jeanty

[11] 4,164,582
[45] Aug. 14, 1979

[54] SYNERGISTIC FUNGICIDAL COMPOSITIONS

[75] Inventor: Pontus A. Harju-Jeanty, Sepänkylä, Finland

[73] Assignee: Kemira Oy, Helsinki, Finland

[21] Appl. No.: 783,441

[22] Filed: Mar. 31, 1977

[30] Foreign Application Priority Data

Apr. 13, 1976 [FI] Finland ................... 761002

[51] Int. Cl.$^2$ ................ A01N 9/22; A01N 9/00; A01N 9/12
[52] U.S. Cl. ................ 424/273 R; 424/276
[58] Field of Search ................ 424/273, 276

[56] References Cited

U.S. PATENT DOCUMENTS

| | | | |
|---|---|---|---|
| 3,249,499 | 5/1966 | Schmeling et al. | 424/276 |
| 3,538,225 | 11/1970 | Dudarevitch et al. | 424/276 |
| 3,657,443 | 4/1972 | Klopping | 424/273 |
| 3,852,460 | 12/1974 | Littler et al. | 424/273 |
| 4,046,906 | 9/1977 | Frensch et al. | 424/273 |
| 4,055,652 | 11/1977 | Walker | 424/273 |

FOREIGN PATENT DOCUMENTS 2063857  7/1971  Fed. Rep. of Germany.

Primary Examiner—Albert T. Meyers
Assistant Examiner—D. W. Robinson
Attorney, Agent, or Firm—Bucknam and Archer

[57] ABSTRACT

A fungicide, especially for the dressing of cereal seeds, which contains: methylbenzimidazole-2-ylcarbamate and 1-[β-(allyloxy)-2,4-dichlorophenethyl]imidazole, phenylcarbamoyl-1,4-oxatine or 1,2-di-(3-methoxycarbonyl-2) or methylbenzimidazole-2-ylcarbamate or 1-[β-(allyloxy)-2,4-dichlorophenethyl]imidazole and at least two compounds selected from 2-pyridinethiol-1-oxide, zinc dimethyldithiocarbamate, 2,3-dihydro-6-methyl-5-phenylcarbamoyl-1,4-oxatine, 1,2-di-(3-methoxycarbonyl-2-thioureido)benzene, and the salts of the same.

2 Claims, No Drawings

SYNERGISTIC FUNGICIDAL COMPOSITIONS

BACKGROUND OF THE INVENTION

The present invention relates to a fungicide, especially to a fungicidal composition intended for the treatment of cereal seeds.

Methylbenzimidazole-2-ylcarbamate is a known systemic fungicide, which is used for protecting fruits, vegetables, cereals, and decorative plants against pathogenic micro-organisms and has the formula

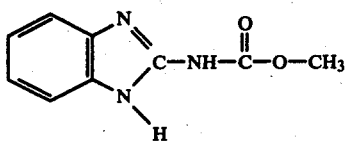

The area of application of also previously known 1-[β-(allyloxy)-2,4-dichlorophenethyl]imidazole is the same; in the formula below it appears as a nitrate:

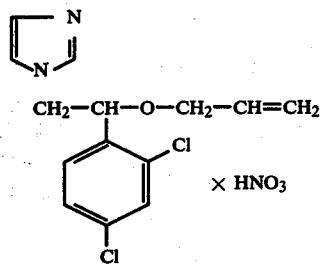

2-pyridinethiol-1-oxy salts have also been used as fungicides and bactericides, but mainly in the cosmetic industry, e.g., in shampoos against dandruff. The formula below represents its zinc salt, zinc pyrithione

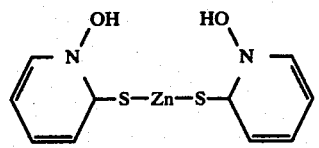

Zinc dimethyldithiocarbamate is used as a fungicide for fruits and vegetables, and its formula is

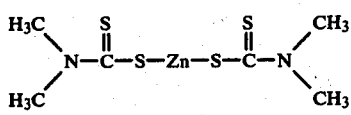

2,3-dihydro-6-methyl-5-phenylcarbamoyl-1,4-oxatine is a systemic fungicide, which is used for vegetables, cotton, and cereals, and its chemical formula is

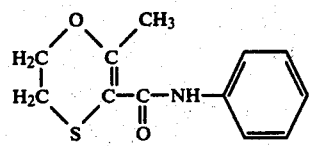

1,2-di-(3-methoxycarbonyl-2-thioureido)benzene is also a systemic fungicide, which is used for protecting fruits, vegetables, cereals, and decorative plants against pathogenic micro-organisms and has the formula

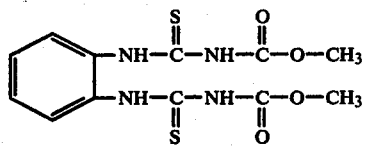

The object of the present invention is therefore to provide a suitable fungicide especially for warding off cereal diseases, for treating cereal seeds or the soil, its effect being primarily directed against fungi passing via the seeds and against soil fungi causing plant diseases. Such fungi include Helminthosporium in barley and oats, Fusarium in rye, and Ustilaginales, i.e. loose smut in oats and bund in wheat.

Using mercury-bearing compositions, such as methoxyethyl mercury salts, for treating seed, good results are obtained in warding off the most important fungi injurious to cereals, with the possible exception of Ustilago avena. These fungicides have, however, several significant harmful properties relating to their poisonous nature, their accumulation in organisms, and the environmental circulation of mercury. For this reason attempts have been made to find new, mercury-free agents to replace mercury-bearing fungicides. Agents so far proposed have, however, relatively limited spectra, and in the treatment of cereal seeds, for example, they do not cover plant diseases which can appear in several cereal species simultaneously.

SUMMARY OF THE INVENTION

Surprisingly it has now been observed that a far greater effect is achieved than the sum effect of the individual components when a fungicide is used which contains: methylbenzimidazole-2-ylcarbamate and 1-[β-(allyloxy)-2,4-dichlorophenethyl]imidazole, phenylcarbamoyl-1,4-oxatine or 1,2di-(3-methoxycarbonyl-2) or methylbenzimidazole-2-ylcarbamate or 1-[β-(allyloxy)-2,4-dichlorophenethyl]imidazole and at least two compounds selected from 2-pyridinethiol-1-oxide, zinc dimethyldithiocarbamate, 2,3-dihydro-6-methyl-5-phenylcarbamoyl-1,4-oxatine, 1,2-di-(3-methoxycarbonyl-2-thioureido)benzene, and the salts of the same. In addition, a sufficiently broad spectrum is also achieved, covering the above diseases of barley, oats, rye, and wheat. Thus a single fungicide can be used to protect cereals against all the most serious fungus diseases threatening them. At the same time a product is obtained which is decisively more advantageous than mercury-bearing fungicides in terms of its poisonous nature and environmental protection.

DESCRIPTION OF THE INVENTION

In investigations, methylbenzimidazole-2-ylcarbamate and 1,2-di-(3-methoxycarbonyl-2-thioureido)benzene proved to be effective against Fusarium culmorum in rye, zinc dimethyldithiocarbamate and 2,3-dihydro-6-methyl-5-phenylcarbamoyl-1,4-oxatine against Helminthosporium gramineum in barley, and sodium-2-pyridinethiol-1-oxide against both Helminthosporium gramineum in barley and Ustilago avena in oats.

1-[β-(allyloxy)-2,4-dichlorophenethyl]imidazole strongly enhances the effect of methylbenzimidazole-2-ylcarbamate against both Helminthosporium gramineum in barley and Fusarium culmorum in rye. Further, 2-pyridinethiol-1-oxide enhances the effect of 1-[β-(allyloxy)-2,4-dichlorophenethyl]imidazole, methylbenzimidazole-2-ylcarbamate, and a mixture of the two against Helminthosporium gramineum in barley and, with the exception of a mixture of 2-pyridinethiol-1-oxide and methylbenzimidazole-2-ylcarbamate, against Fusarium gramineum in rye. Further, 1,2-di-(3-methoxycarbonyl-2-thioureido)benzene and zinc dimethyldithiocarbamate enhance the effect of 1-[β-(allyloxy)-2,4-dichlorophenethyl]imidazole and zinc dimethyldithiocarbamate enhances the effect of a mixture of 1-[β-(allyloxy)-2,4-dichlorophenethyl]imidazole and methylbenzimidazole-2-ylcarbamate against Helminthosporium gramineum in barley. 1,2-di-(3-methoxycarbonyl-2-thioureido)benzene, zinc dimethyldithiocarbamate and 2,3-dihydro-6-methyl-5-phenylcarbamoyl-1,4-oxatine enhance the effect of methylbenzimidazole-2-ylcarbamate and its mixture with 1-[β-(allyloxy)-2,4-dichlorophenethyl]imidazole, and 2,3-dihydro-6-methyl-5-phenylcarbamoyl-1,4-oxatine enhances the effect of 1-[β-(allyloxy)-2,4-dichlorophenethyl]imidazole against Fusarium culmorum in rye. These synergistic qualities are illustrated in the effect determination examples below.

The active ingredients according to the invention can be produced in different forms, such as solutions, emulsion concentrates, suspensions, powders, pastes, and granules. The forms in which they are used depend entirely on the purpose for which they are used. They are manufactured by known methods, e.g., by mixing together active ingredients and additives, i.e., liquid solvents, gases liquefying under pressure, and/or solid carrier substances, possibly using surface active agents, i.e., emulsifiers and/or dispersing agents and/or frothing agents. If water is used as an additive, organic solvents, for example, can be used as auxiliary solvents. It is, however, also possible to manufacture concentrates, suitable for being diluted with water, composed of an active ingredient, an emulsifying or dispersing agent and possibly a solvent. Possible liquid solvents include in particular aromatic solvents such as xylene, toluene, benzene, or alkylnaphthalene; chlorinated aromatic or chlorinated aliphatic hydrocarbons such as chlorobenzene, chlorethylene, or methylene chloride; aliphatic hydrocarbons such as cyclohexane or paraffins, e.g., petroleum fractions; alcohols such as buthanol and glycol as well as their ethers and esters; ketones such as acetone, methylethyl ketone, or cyclohexanone; strongly polar solvents such as dimethyl formamide and dimethyl sulfoxide; and water. Substances that can be used as solid carriers include natural stone powder such as kaolin, clay earth, talc, chalk, quartz, attapulgite, montmorrilonite, or diatomite, and synthetic stone powder such as high-dispersity silicic acid, aluminum oxide, and aluminum silicate. Emulsifiers suitable for use include polyoxyethylene fatty acid esters and ethers, alkyl and aryl sulfonates, and alkyl sulfates. Lignin, sulfite waste liquor, and methyl cellulose are typical examples of the dispersing agents. Other known active ingredients, such as herbicides, insecticides, fungicides, and growth controllers, as well as nutrients or soil-improving agents, can also be added to the active ingredient combinations according to the invention.

A fungicide according to the invention usually contains active ingredients 2–90% by weight, preferably 10–70% by weight, out of which the proportion of methylbenzimidazole-2-ylcarbamate is usually 10–99% by weight, preferably 60–97% by weight, the proportion of 1-[β-(allyloxy)-2,4-dichlorophenethyl]imidazole 1–70% by weight, preferably 3–40% by weight, the proportion of sodium-2-pyridinethiol-1-oxide 5–90% by weight, preferably 30–80% by weight, and the proportion of each of zinc dimethyldithiocarbamate, 2,3-dihydro-6-methyl-5-phenylcarbamoyl-1,4-oxatine and 1,2-di-(3-methoxycarbonyl-2-thioureido) benzene 5–99% by weight, preferably 20–97% by weight. In a double composition the distribution of the effective ingredients is usually 1–90% by weight: 10–99% by weight, preferably 3–40% by weight: 97–97% by weight between 1-[β-(allyloxy)-2,4-dichlorophenethyl]imidazole and zinc dimethyl-dithiocarbamate, 2,3-dihydro-6-methyl-5-phenylcarbamoyl-1,4-oxatine, 1,2-di-(3-methoxycarbonyl-2-thioureido) benzene or methylbenzimidazole-2-ylcarbamate; 10–90% by weight: 10–90% by weight, preferably 30–80% by weight: 20–70% by weight between methylbenzimidazole-2-ylcarbamate and 2-pyridinethiol-1-oxide, zinc dimethyldithiocarbamate, 2,3-dihydro-6-methyl-5-phenylcarbamoyl-1,4-oxatine or 1,2-di-(3-methoxycarbonyl-2-thioureido) benzene; and 1–70% by weight: 30–99% by weight, preferably 3–40 by weight: 60–97% by weight between 1-[β-(allyloxy)-2,4-dichlorophenethyl]imidazole and 2-pyridinethiol-1-oxide.

The fungicide is used in the conventional manner, e.g., by dusting, spraying, spreading, strewing, watering, or by dry dressing, sludge dressing, wet dressing, or damp dressing of seeds. In the dressing of seeds the product is generally used at a rate of 100–400 g or 100–400 ml per 100 kg of cereal seed, i.e., generally 20 mg–3.6 g of active ingredients per one kg of cereal seed; the recommended rate is 100 mg–2.8 g per one kg of cereal seed.

The invention is described below in more detail by way of examples.

EXAMPLE 1

Experiment on barley with Helminthosporium gramineum.

Seeds of barley were sterilized in a 1-percent sodium hypochlorite solution (½–1 h), dried, and mixed with 5-day-old Helminthosporium gramineum growths with their agars (Bacto potato dextrose agar) and closed in a vacuum desiccator (water suction) for 24 h. The seeds were allowed to dry and the agar was removed, after which the contaminated seeds were ready for use. The effectiveness determination was performed according to the "Ulster method"; the contaminated seeds were dressed and 10 seeds were placed with tweezers sterilely onto a nutritive medium in a Petri dish. 10 seeds which had not been dressed were placed as controls on a nutritive medium. 5 parallel determinations were performed on each specimen.

The nutritive medium used in the effect determinations was Bacto potato dextrose agar, and 200 mg or 0.2 ml of the dressing agent per 100 g of seeds was used for the dressing of the seeds. The Petri dishes were incubated for 5 days at +24° C., and the dressed seeds were then examined after one, three, five, and eight weeks and six months after the dressing. In the examples the examinations were performed 5 weeks after the dressing. The effect of the dressing agent was calculated as a percentage according to Abbotsh's formula below:

$$\text{effect \%} = \frac{\substack{\text{number of seeds} \\ \text{contaminated} \\ \text{among controls}} - \substack{\text{number of seeds} \\ \text{contaminated in} \\ \text{experiment}}}{\substack{\text{number of seeds} \\ \text{contaminated} \\ \text{among controls}}} \times 100$$

The results are given in Table 1 below.

and zinc dimethyldithiocarbamate; methylbenzimidazole and 2,3-dihydro-6-methyl-5-phenylcarbamoyl-1,4-oxatine, 1-[β-(allyloxy)-2,4-dichlorophenethyl]imidazole and 1,2-di-(3-methoxycarbonyl-2-thioureido)benzene; as well as 1-[β-(allyloxy)-2,4-dichlorophenethyl]imidazole and zinc dimethylcarbamate, enhance each other's effect, i.e., they act synergistically. The superiority of the compositions according

TABLE I

| Series 1: Dressing agent | Dressing agent per 100 g of seeds | Effect % 2 weeks after dressing |
|---|---|---|
| Methylbenzimidazole-2-ylcarbamate (50% WP) = Agent A | 0.2 g | 8 |
| 1-[β-(allyloxy)-2,4-dichlorophenethyl]imidazole (33.3 g/l) = Agent B | 0.2 ml = 0.193 g 0.2 g* | 18 |
| Sodium salt of 2-pyridine-thiol-1-oxide (20%) = Agent C | 0.2 g | 90 |
| Zinc salt of 2-pyridine-thiol-1-oxide (10%) = Agent D | 0.2 ml = 0.206 g** 0.2 g | 92 |
| Agent A + Agent B = 2:1 | 0.133 g + 0.067 g = 0.2 g | |
| Agent A + Agent B = 1:2 | 0.067 g + 0.133 ml = 0.067 + 0.128 g = 0.195 g ≈ 0.2 g | 44 |
| Agent A + Agent C = 1:2 | 0.067 g + 0.133 g | 48 |
| Agent B + Agent D = 1:2 | 0.064 g + 0.137 g = 0.198 g 0.2 g | 92 |
| Agent A + Agent B + Agent C = 2:2:1 | 0.08 g + 0.08 ml*** + 0.04 g = 0.08 g + 0.077 g + 0.04 g = 0.197 g ≈ 0.2 g | 96 98 |
| Agent A + Agent B + Agent C = 2:1:2 | 0.08 g + 0.04 ml + 0.08 g = 0.08 g + 0.028 g + 0.08 g = 0.188 g ≈ 0.2 g | 98 |

| Series 2: Dressing agent | Dressing agent per 100 g of seeds | Effect % 1 week after dressing |
|---|---|---|
| Methylbenzimidazole-2-ylcarbamate (50% WP) = Agent A | 0.2 g | 68 |
| 1-[β-(allyloxy)-2,4-dichlorophenethyl]imidazole (3.3%) = Agent B | 0.2 g | 48 |
| 1,2-di-(3-methoxycarbonyl-2-thioureido)benzene (70% WP) = Agent E | 0.2 g | 52 |
| 2,3-dihydro-6-methyl-5-phenylcarbamoyl-1,4-oxatine (75% WP) = Agent F | 0.2 g | 90 |
| Zinc dimethyldithiocarbamate (100%) = Agent G | 0.2 g | 96 |
| Agent A + Agent B = 1:1 | 0.1 g + 0.1 g | 72 |
| Agent A + Agent B + Agent G = 2:2:1 | 0.08 g + 0.08 g + 0.04 g | 98 |
| Agent A + Agent F = 1:2 | 0.067 g + 0.133 g | 94 |
| Agent B + Agent E = 2:1 | 0.133 g + 0.067 g | 88 |
| Agent B + Agent G = 1:1 | 0.1 g + 0.1 g | 98 |

Control agents:
Methoxyethylmercury chloride (2.21%) 0.2 g 46
Methoxyethylmercury acetate (18.4 g/l) 0.194 g 44 ≈ 0.2 g.

*Specific gravity of Agent B is 0.964
**Specific gravity of Agent D is 0.1.032
***0.08 ml is equal to 0.077 g The example and Table 1 clearly show how methylbenzimidazole-2-ylcarbamate and 1-[β-(allyloxy)-2,4-dichlorophenylethyl]imidazole; methylbenzimidazole-2-ylcarbamate and, 2-pyridinethiol-1-oxide; 1-[β-(allyloxy)-2,4-dichlorophenethyl]imidazole and 2-pyridinethiol-1-oxide (S=suspension); methylbenzimidazole-2-ylcarbamate (WP=Spray powder), 1-[β-(allyloxy)-2,4-dichlorophenethyl]imidazole and 2-pyridinethiol-1-oxide; methylbenzimidazole-2-ylcarbamate, 1-[β-(allyloxy)-2,4-dichlorophenethyl]imidazole to the invention over the mercury-bearing seed dressing agents currently used can also be observed.

EXAMPLE 2

Seed dressing experiment on rye with Fusarium culmorum.

Rye seeds were sterilized in a 1-percent sodium hypochlorite solution. After drying they were mixed with a strong-growth myceliumagar mass which had been obtained by growing Fusarium culmorum for 15 days in the dark at room temperature. This damp mass containing the seeds was spread into damp-proof dishes and allowed to stand for a couple of days in the dark at room temperature. Then the seeds were allowed to dry and the agar was detached from them. The seed dressing and effect determination were performed as in Example 1, except that the nutritive medium used was malt agar and the incubation took place in the dark at room temperature for 5 days. The results are shown in Table 2 below.

TABLE 2

| Series 2: Dressing agent | Dressing agent per 100 g of seeds | Effect % 5 weeks after dressing |
|---|---|---|
| methylbenzimidazole-2-ylcarbamate (50% WP) = Agent A | 0.2 g | 88 |
| 1-[β-(allyloxy)-2,4-dichlorophenethyl] imidazole (33.3 g/l) = Agent B | 0.2 ml = 0.193 g ≈ 0.2 g | 12 |
| Sodium salt of 2-pyridine-thiol-1-oxide (80%) = Agent C | 0.2 g | 28 |
| Zinc salt of 2-pyridine-thiol-1-oxide (10%) = Agent D | 0.2 ml = 0.206 g ≈ 0.2 g | 4 |
| Agent A + Agent B = 2:1 | 0.133 g + 0.067 ml = 0.133 + 0.064 g = 0.197 g ≈ 0.2 g | 92 |
| Agent A + Agent B = 1:2 | 0.067 g + 0.133 ml = 0.067 + 0.128 g = 0.195 g ≈ 0.2 g | 90 |
| Agent B + Agent C = 2:1 | 0.133 ml + 0.067 g | 74 |
| Agent B + Agent D = 1:1 | 0.1 ml + 0.1 ml = 0.1 + 0.103 g = 0.203 g ≈ 0.2 g | 60 |
| Agent A + Agent B + Agent C = 2:2:1 | 0.08 g + 0.08 ml + 0.04 g | 96 |
| Agent A + Agent B + Agent C = 2:1:2 | 0.08 g + 0.04 ml + 0.08 g | 94 |
| Series 2: Dressing agent | Dressing agent per 100 g of seeds | Effect % 1 week after dressing |
| Methylbenzimidazole-2-ylcarbamate (50% WP) = Agent A | 0.2 g | 80 |
| 1-[β-(allyloxy)-2,4-dichlorophenethyl] imidazole (3.3%) = Agent B | 0.2 g | 42 |
| 1,2-di-(3-methoxycarbonyl-2-thioureido)benzene (70% WP) = Agent E | 0.2 g | 88 |
| 2,3-dihydro-6-methyl-5-phenylcarbamoyl-1,4-oxatine (75% WP) = Agent F | 0.2 g | 60 |
| Zinc dimethyldithio-carbamate (100%) = Agent G | 0.2 g | 0 |
| Agent A + Agent B = 1:1 | 0.1 g + 0.1 g | 84 |
| Agent A + Agent E = 2:1 | 1.133 g + 0.067 g | 96 |
| Agent A + Agent F = 1:1 | 0.1 g + 0.1 g | 94 |
| Agent A + Agent G = 2:1 | 0.133 g + 0.067 g | 96 |
| Agent B + Agent F = 2:1 | 0.133 g + 0.067 g | 76 |
| Agent A + Agent B + Agent E = 2:2:1 | 0.08 g + 0.08 g + 0.04 g | 94 |
| Agent A + Agent B + Agent F = 2:2:1 | 0.08 g + 0.08 g + 0.04 g | 90 |
| Control agents | | |
| Methoxyethylmercury chloride (2.21%) 0.2 g 0 | | |
| Methoxyethylmercury acetate (18.4 g/l)0.2 ml 0 | | |

As with Helminthosporium gramineum in barley, the results with Fusarium culmorum in rye were also effective, and they clearly show the synergistic effect of the active agents in a fungicide according to the invention (Example 2). Combinations in which the agents enhance each other's effect are: methylbenzimidazole-2-ylcarbamate+1-[β-(allyloxy)-2,4-dichlorophenethyl-]imidazole, methylbenzimidazole-2-ylcarbamate+1-[β-(allyloxy)-2,4-dichlorophenethyl]imidazole+2-pyridinethiol-1-oxide, 1-[β-(allyloxy)-2,4-dichlorophenethyl]imidazole+2-pyridinethiol-1-oxide, methylbenzimidazole-2-ylcarbamate+1,2-di-(3-methoxycarbonyl-2-thioureido)benzene, methylbenzimidazole-2-ylcarbamate +2,3-dihydro-6-methyl-5-pheneylcarbamoyl-1,4-oxatine, methylbenzimidazole-2-ylcarbamate+1-[β-(allyloxy)-2,4-dichlorophenethyl-]imidazole+1,2-di-(3-methoxycarbonyl-2-thioureido) benzene, and methylbenzimidazole-2-ylcarbamate+1-[β-(allyloxy)-2,4-dichlorophenethyl]imidazole+2,3-dihydro-6-methyl-5-phenylcarbamoyl-1,4-oxatine. The superiority of the compositions according to the invention over the control agents is obvious.

EXAMPLE 3

Experiment on oats with Ustilago avena.

Oats seeds were contaminated with sifted spori of Ustilago avena loose smut, which had been mixed with a nutritive solution containing (NH$_4$)$_2$SO$_4$, K$_2$SO$_4$, KH$_2$PO$_4$, glucose, MgSO$_4$, NaCl, and CaCl. After vacuum treatment and drying, the seeds were placed for 24 h at a temperature of +25° C. and at a humidity of 100% and then dried, after which they were ready for dressing. Seed dressing agent was used at a rate of 300 mg/100 g of oats seeds. A layer of damp cotton was placed in a sterile germination dish (200 ml of sterile water/dish) and on top of the cotton a sheet of sterile blotting paper was laid, on which 50 dressed seeds were placed. Another sheet of damp sterile blotting paper was placed on top of the seeds. The dish was closed and incubated at room temperature in the dark for 3 weeks. The effect percentage was calculated as in Example 1 and is given below in Table 3.

TABLE 3

| Dressing agent | Dressing agent per 100 g of seeds | Effect % 5 weeks after dressing |
| --- | --- | --- |
| Sodium salt of 2-pyridine-thiol-1-oxide (40%) | 0.3 g | 100 |
| Tetramethyl-thiouramide sulfide (40% WP) | 0.3 g | 55 |

TABLE 3-continued

| Dressing agent | Dressing agent per 100 g of seeds | Effect % 5 weeks after dressing |
| --- | --- | --- |
| Methoxyethyl-mercury chloride (2.21%) | 0.3 g | 96 |

Table 3 shows the effectiveness of 2-pyridinethiol-1-oxide against Ustilago avena in oats. 2-pyridinethiol-1-oxide is more effective against Ustilago avena than the currently known tetramethylthiouramide sulfide and methoxyethylmercury chloride, and it thus expands the area of use of the compositions according to the invention.

What is claimed is:

1. A fungicidal composition comprising 2–90% by weight of active ingredients, said active ingredients consisting of A methylbenzimidazole-2-ylcarbamate or one of its salts, and B 1-[β-(allyloxy)2,4-dichlorophenethyl]imidazole or one of its salts wherein said ingredients A and B are in the proportion within the range between 2:1 and 1:2 and an agriculturally acceptable carrier.

2. The composition according to claim 1 additionally comprising 2,3-dihydro-6-methyl-5-phenylcarbamoyl-1,4-oxatine in the amount of 20–97% of the total composition.

* * * * *